United States Patent [19]
Caizza

[11] Patent Number: 5,964,737
[45] Date of Patent: *Oct. 12, 1999

[54] MEDICATION TRANSFER CONNECTOR AND CONNECTION

[75] Inventor: Richard J. Caizza, Barry Lakes, N.J.

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/104,711

[22] Filed: Jun. 25, 1998

[51] Int. Cl.⁶ .................................................. A61M 5/00
[52] U.S. Cl. ........................... 604/239; 604/187; 604/272
[58] Field of Search .................................... 604/181, 187, 604/218, 239, 240, 243, 264, 272, 241, 256

[56] References Cited

U.S. PATENT DOCUMENTS

| | | | |
|---|---|---|---|
| 4,187,848 | 2/1980 | Taylor | 128/247 |
| 5,573,516 | 11/1996 | Tyner | 604/249 |
| 5,746,728 | 5/1998 | Py | 604/298 |
| 5,792,099 | 8/1998 | DeCamp et al. | 604/51 |
| 5,902,277 | 5/1999 | Jentzen | 604/218 |

Primary Examiner—Wynn Wood Coggins
Assistant Examiner—LoAn H. Thanh
Attorney, Agent, or Firm—Keith J. McWha

[57] ABSTRACT

A medication transfer connector and connection is described which allows dead-space reduction in the fluid path between a first and a second fluid transfer device. The reduction in dead-space does not depend on manufacturing dimensional tolerances of the transfer device's or connector's mating components. Thus, waste of medication due to dead-space is reduced without depending on control of manufacturing tolerances of the mating components' dimensions. Selection and interchange of the first and second fluid transfer devices are allowed.

11 Claims, 12 Drawing Sheets

MEDICATION TRANSFER CONNECTOR AND CONNECTION

FIELD OF THE INVENTION

This invention relates generally to an improved medication transfer connector and connection between two fluid transfer devices. More particularly, this invention relates to reducing the dead-space between the connection of a syringe assembly and a needle hub.

BACKGROUND OF THE INVENTION

Hypodermic syringes are well known to be used to deliver medication to patients. A traditional hypodermic syringe typically includes a syringe barrel having opposed proximal and distal ends. A cylindrical chamber wall extends between the ends and defines a fluid-receiving chamber. The proximal end of the traditional syringe barrel is substantially open and receives a plunger in sliding fluid-tight engagement. The distal end of the traditional syringe barrel includes a passage communicating with the chamber. A needle cannula is mounted to the distal end of the traditional syringe barrel such that the lumen of the needle cannula communicates with the passage in the chamber of the syringe barrel. Movement of the plunger in the proximal direction draws fluid through the lumen of the needle cannula and into the chamber. Movement of the plunger in a proximal to distal direction urges fluid from the chamber and through the lumen of the needle cannula.

The traditional syringe is designed for a variety of clinical operations. Many applications require needle changing or connection of the syringe to items such as stopcocks or tubing sets. Typically, traditional syringes create a dead-space between the connection of the syringe and the needle hub. These traditional syringes often trap and waste a certain amount of medication in the dead-space after injection. The amount of drug that is not expelled after injection and remains trapped in the fluid transfer connection is wasted when the syringe is discarded.

A typical traditional hypodermic syringe has three major components: (i) a syringe barrel; (ii) a plunger rod; and (iii) a stopper. Each of the three major components are described more completely below. As previously stated, hypodermic syringes contain a certain amount of dead-space between the connection of the syringe barrel and needle hub. This dead-space has been shown to cause waste of medication as well as added expense. The increase in cost is exacerbated when expensive drugs are delivered to the patient.

Attempts to reduce the dead-space between the syringe barrel and the needle hub in the traditional syringe are aggravated by the tight manufacturing tolerances of the mating components' dimensions required to minimize the dead-space. In addition, use of various syringe barrels and needle hubs from different manufacturers, which operate under different manufacturing tolerances of the above mating components' dimensions, can create an even more difficult situation to hold the dead space to a bare minimum.

Therefore, advancements in hypodermic syringes to reduce dead-space are still dependent on manufacturing tolerances of the mating components' dimensions. Thus, while some prior art hypodermic syringes attempt to reduce the dead-space and save medication costs, the dead-space still varies with the manufacturing tolerances of the mating components' dimensions. There is still a need for an improved fluid transfer connection between the syringe barrel and needle hub that will reduce the dead-space and remain independent of manufacturing tolerances of the mating components' dimensions.

SUMMARY OF THE INVENTION

A medication transfer connector for reducing dead-space volume in a fluid path between a first fluid transfer device which delivers medication and a second fluid transfer device, comprises a hub and a resilient member. The hub has an open end, a end, and a conduit therethrough. The open end is for receiving the first fluid transfer device. The open end also has a surface defining a cavity. The closed end of the hub is attached to the second fluid transfer device such that the conduit of the hub is in fluid communication with the second fluid transfer device. The resilient member is for reducing the dead-space volume.

The resilient member has a first end, a second end, an outside surface and a channel therethrough. The resilient member is disposed in the hub's cavity. The first end of the resilient member is exposed to the hub's cavity. Portions of the outside surface of the resilient member form a seal about the surface of the hub's open end. When the hub is attached to the first fluid transfer device, a second seal is created between the resilient member's first end and the first fluid transfer device. The channel and the resilient member is in fluid communication with the first fluid transfer device and hub's conduit. During attachment, the resilient member is compressed. The dead-space volume in the fluid path between the fluid transfer devices is thereby reduced.

In another embodiment, the resilient member can further comprise at least one external locking rib, and the surface of the open end of the hub can further comprise at least one internal locking rib. The external and internal locking ribs are adjacent to each other facilitating mounting of the resilient member to the hub. The above medication transfer connector can have a cavity that is conical and a resilient member that is tapered.

In another embodiment, the medication transfer connector can have a resilient member that is fixably attached to the first fluid transfer device. The resilient member can be made of an elastomeric material.

The medication transfer connector in another embodiment, comprises a resilient member that is a coil spring assembly. The coil spring assembly has a coil spring and a resilient sheath. The resilient sheath covers the coil spring. The coil spring assembly is fixably attached to the cavity of the hub such that when attached, the medication delivered by the first fluid transfer device flows through the coil spring. The resilient sheath prevents the medication from escaping and guides the medication through the hub's conduit. The coil spring assembly can further comprise a locating ring with a passage therethrough for alignment of the coil spring assembly with the first fluid transfer device. The locating ring is adjacent the coil spring. The passage of the locating ring is in fluid communication with the hub's conduit. Alternatively, the coil spring assembly can be fixably attached to the first fluid transfer device instead of the hub's cavity.

In another embodiment, the second fluid transfer device can be replaced with a piercing member having a proximal end, a distal end, and a lumen therethrough. The end of the hub is attached to the proximal end of the piercing member so that the hub's conduit is in fluid communication with the lumen of the piercing member. The piercing member can be a needle cannula, have a blunt distal end, or a sharpened distal end.

Also provided is a medication transfer connection that reduces dead-space volume in a fluid path. The connection comprises a first fluid transfer device for delivering medication, a piercing member, a hub, and an elastomeric plug. The fluid transfer device can be a syringe. The piercing member can be a needle cannula, have a blunt distal end and have a sharpened distal end. Alternatively, the elastomeric plug can be fixably attached to the first fluid transfer device.

These and other aspects, features and advantages of the present invention will become apparent from the following detailed description taken in conjunction with the accompanying drawings.

BRIEF DESCRIPTION OF THE DRAWINGS

FIG. 4 is a longitudinal cross-sectional view of the subject invention taken along line 4—4 in FIG. 2a.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention. It is not intended to limit the scope of the invention to these embodiments illustrated. The scope of the invention will be measured by the appended claims and their equivalents.

Figure 1:
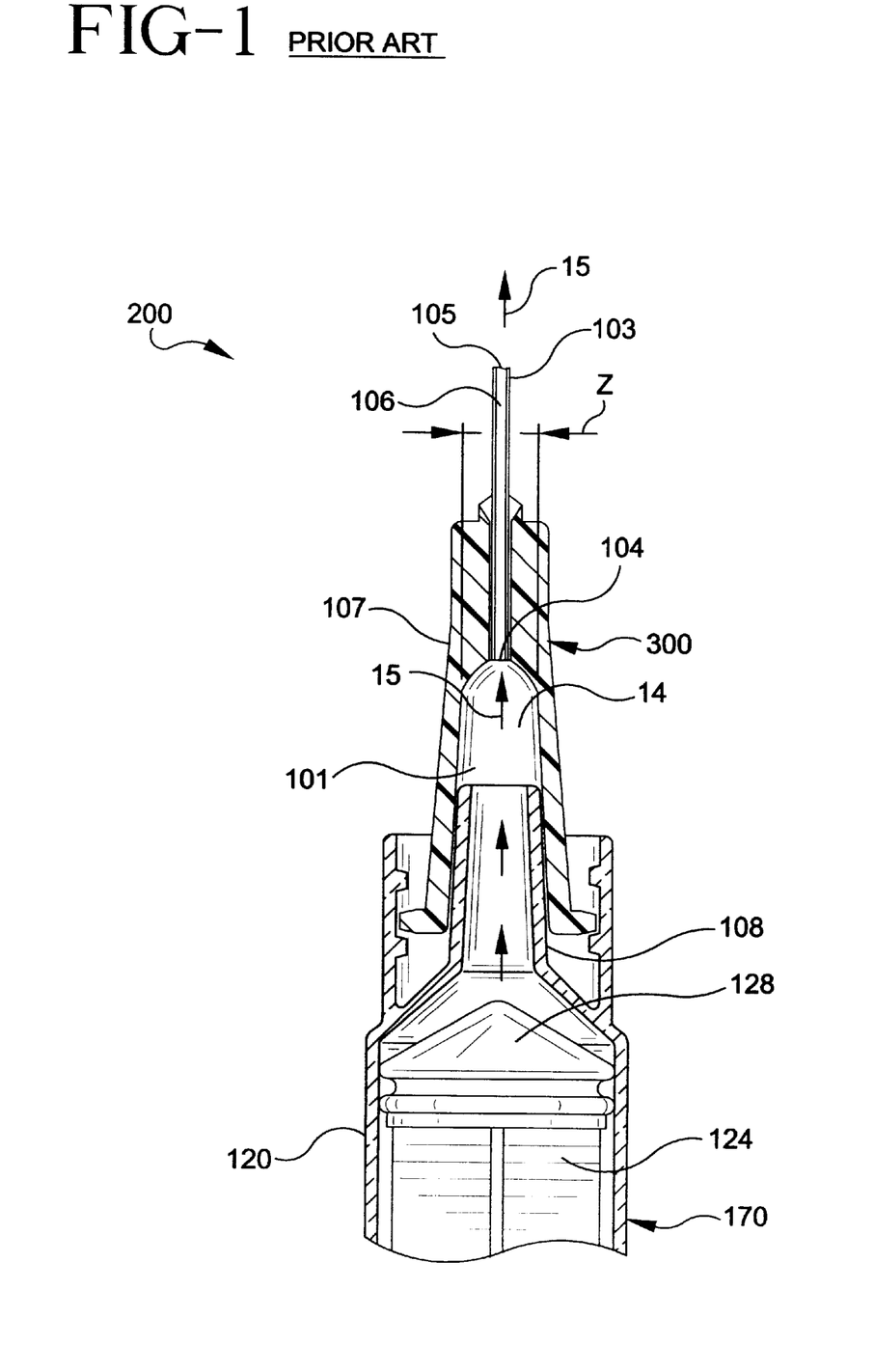
FIG. 1 illustrates dead-space in a prior art medication transfer connector and a hypodermic syringe.

Adverting to the drawings, FIG. 1 illustrates a prior art medication transfer connector 300, a prior art medication transfer connection 200, and the dependency of the prior art on manufacturing tolerances of the mating components' dimensions. Prior art medication transfer connector 300 includes a needle cannula 103 having a proximal end 104, a distal end 105, and a lumen 106 therethrough. Prior art medication transfer connector 300 also includes a needle hub 107 having an inside diameter "Z" and a cavity 101. Cavity 101 receives a luer slip 108 of a prior art syringe 170 thereby forming a prior art medication transfer connection 200. A dead-space volume 14 in fluid path 15 is thereby created as well. The prior art syringe 170 includes a plunger 124, a syringe barrel 120, a stopper 128, and luer slip 108. The prior art syringe is used to deliver medication to the fluid path 15. Control or minimization of dead-space volume 14 in fluid path 15 requires manufacturing control of the tolerances for inside diameter "Z" and luer slip 108.

Typically, prior art syringe 170 creates dead-space volume 14 between the connection of syringe 170 and needle hub 107. This traditional syringe 170 often traps and wastes a certain amount of medication in dead-space volume 14 after injection. The amount of drug that is not expelled after injection and remains trapped in dead space volume 14 is wasted when syringe 170 is discarded.

Dead-space volume 14 has been shown to cause waste of medication as well as added expense. The increase in cost is exacerbated when expensive drugs are delivered to the patient such as tetanus toxoid, influenza virus vaccine, hepatitis B vaccine, and other similar drugs. When even more expensive drugs, such as dialysis-related erythropoietin, or filgrastim or many of the new and proposed recombinant biologicals, are used with prior art syringe 170, medication is wasted in dead-space volume 14 between the luer slip 108 of syringe barrel 120 and needle hub 107. This waste of even more expensive drugs causes even more additional costs.

An advantage of the present invention is that dead-space volume 14 in fluid path 15 as shown in FIGS. 2–8 can be reduced without total dependence on manufacturing tolerances of mating components' dimensions. Components of the present invention can be made by injection molding techniques or other manufacturing techniques known by one skilled in the art. As shown in FIGS. 2–8, a medication transfer connector 56 of the present invention preferably comprises a hub 18, and a resilient member 34. A first fluid transfer device 1 can be attached to the medication transfer connector 56 to form a medication transfer connection 57.

Figure 3:
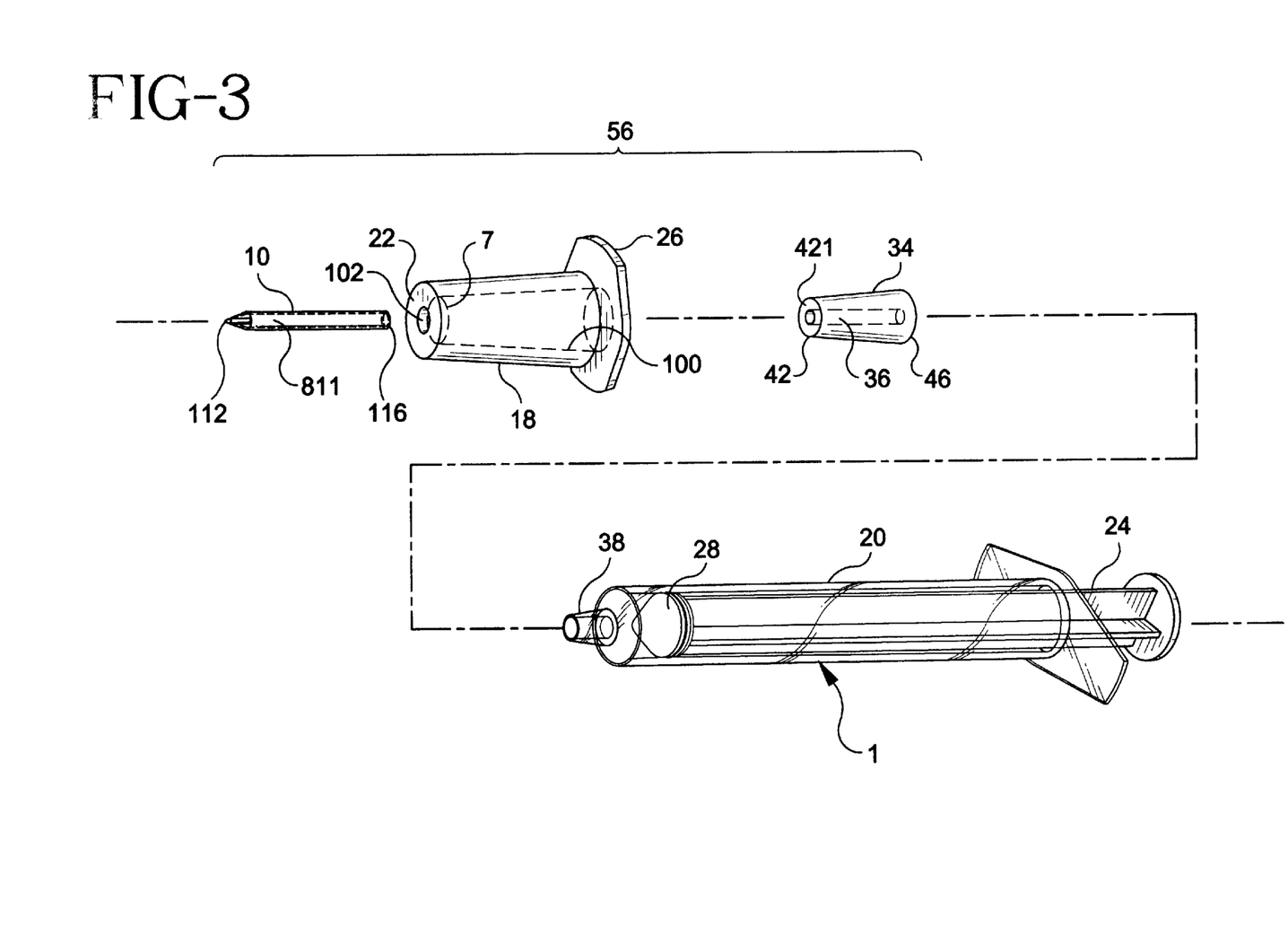
FIG. 3 is an exploded view in perspective of the subject invention.

The first fluid transfer device 1 delivers medication to the connector 56. Preferably, the first fluid transfer device 1 is a syringe 171 as shown in FIG. 3 having a plunger rod 24, a stopper 28, a syringe barrel 20 and a male fitting 38. It is within the purview of this invention for the first fluid transfer device 1 to also be an I.V. bag or assembly, an insulin pump, an injector pen, a syringe or any other medical device which delivers medication through a connector that creates dead-space volume 14 in its fluid path 15 to the patient.

Preferably, the hub 18 is a needle hub 118 as shown in FIG. 3. However, it is within the scope of the present invention that hub 18 may be a pen needle hub, intravenous needle hub, or any other type of medication delivery hub that can create dead-space volume 14 when connected to a male fitting 38.

Figure 2A:
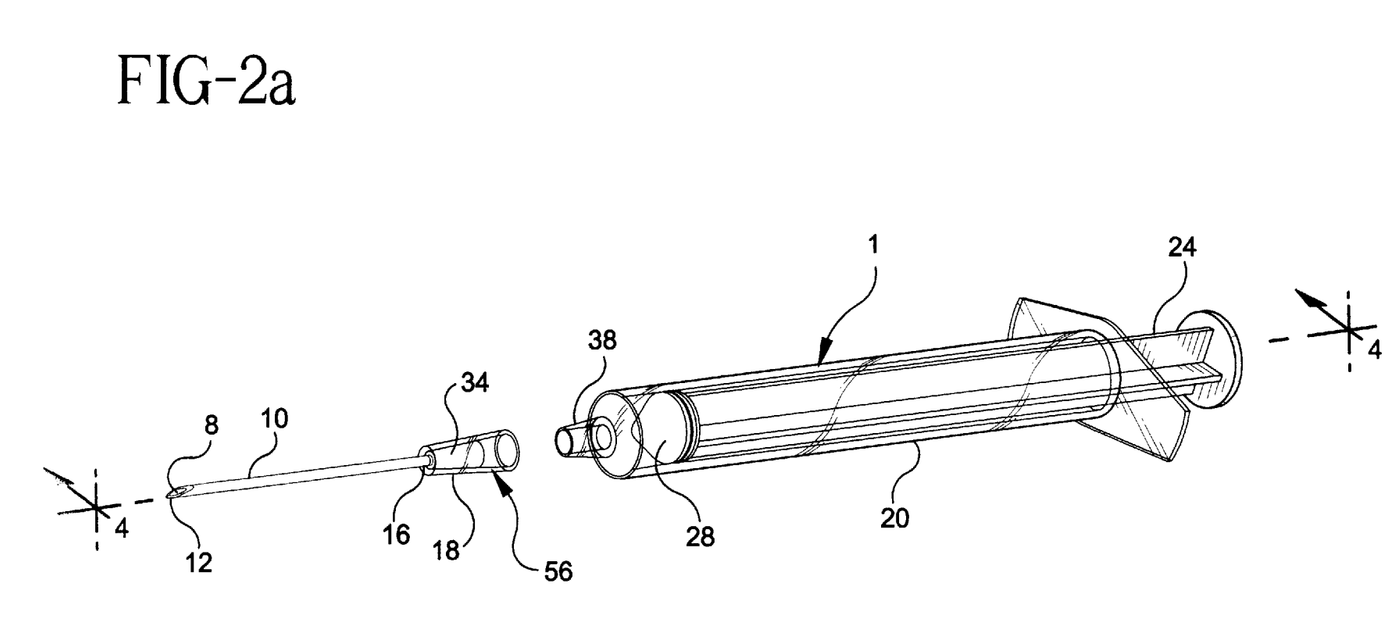
FIG. 2a is a perspective view of the subject invention.
Figure 2B:
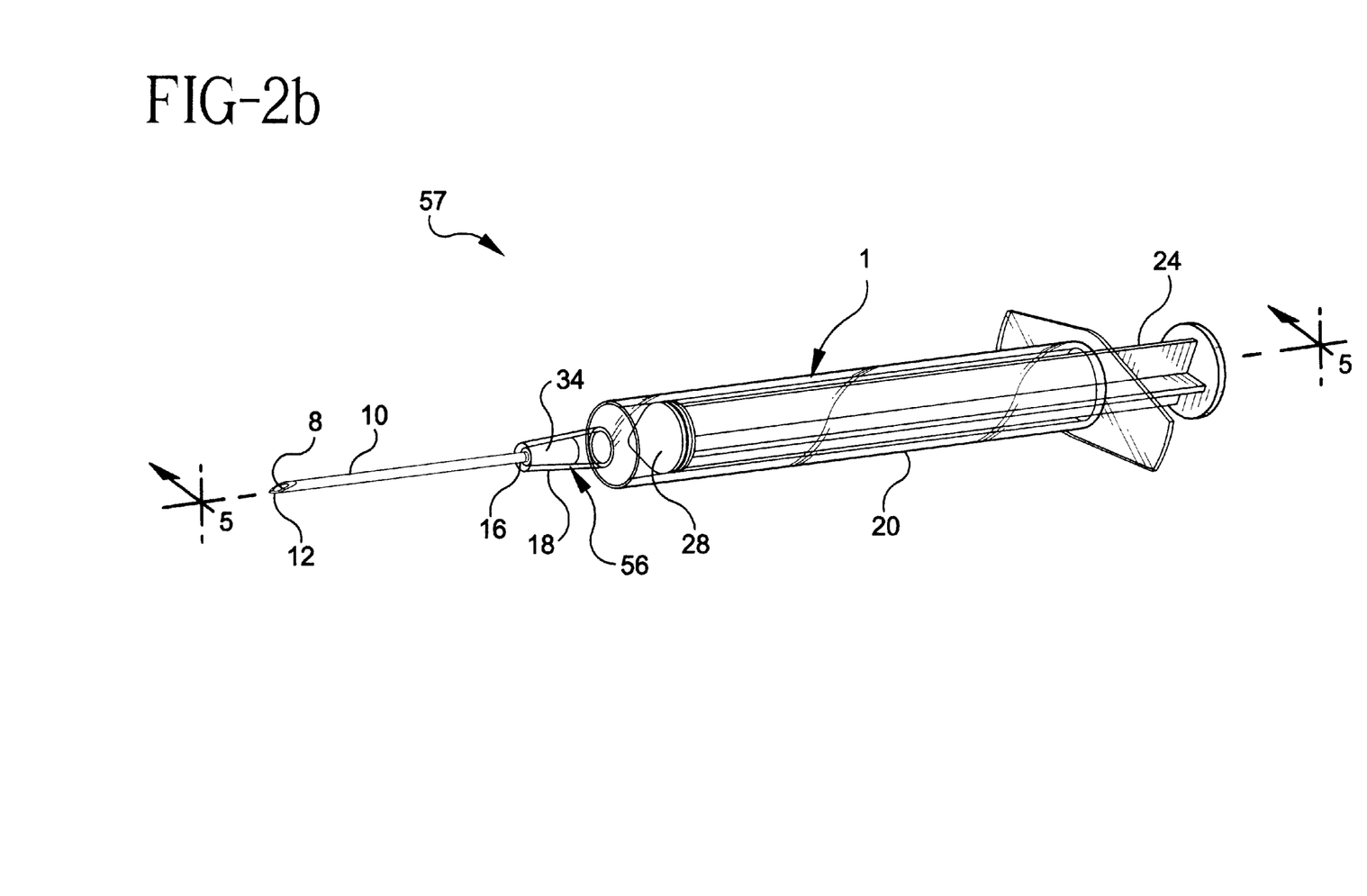
FIG. 2b is a perspective view of the subject invention assembled.

As shown in FIG. 3, the medication transfer connector 56 may also be attached to a second fluid transfer device that delivers the medication to the patient. The second fluid transfer device may be piercing member 10 as shown in FIG. 2 having a distal end 12, a proximal end 16, and a lumen 8 therethrough. Piercing member 10 is used to pierce the skin of a patient to complete fluid path 15 from first fluid transfer device 1 to the patient. Preferably, the second fluid transfer device as shown in FIG. 3 is piercing member 10 having lumen 811. Piercing member 10 can have distal end 112 either blunt or sharpened for delivery of medication to the patient. Piercing member 10 has a lumen 811 therethrough. It is within the scope of the present invention that piercing member 10 may be an I.V. port, catheter, stopcock or any other medical device that delivers medication to a patient and creates dead-space volume in one or more of its connections.

Figure 4:
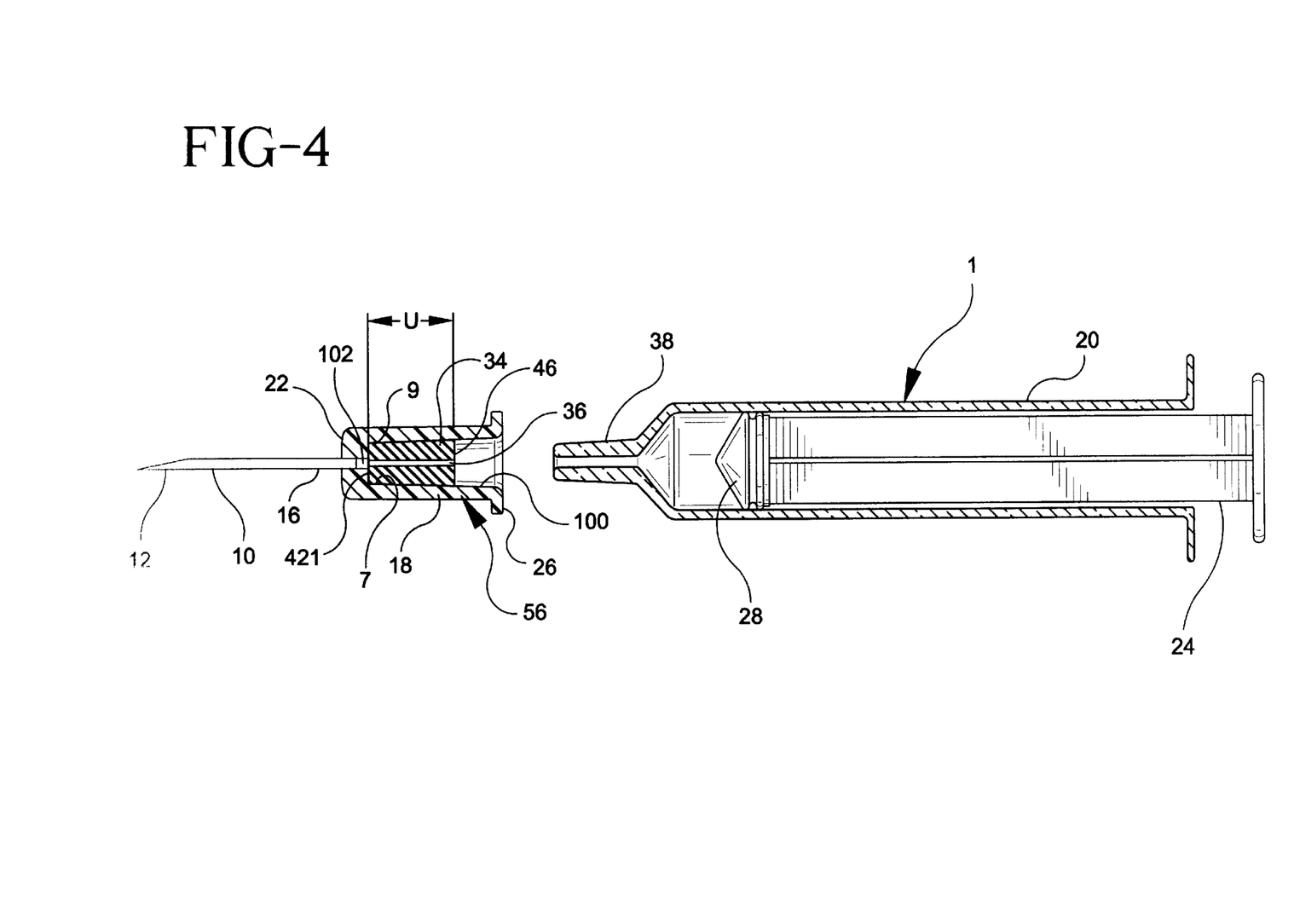
Figure 5:
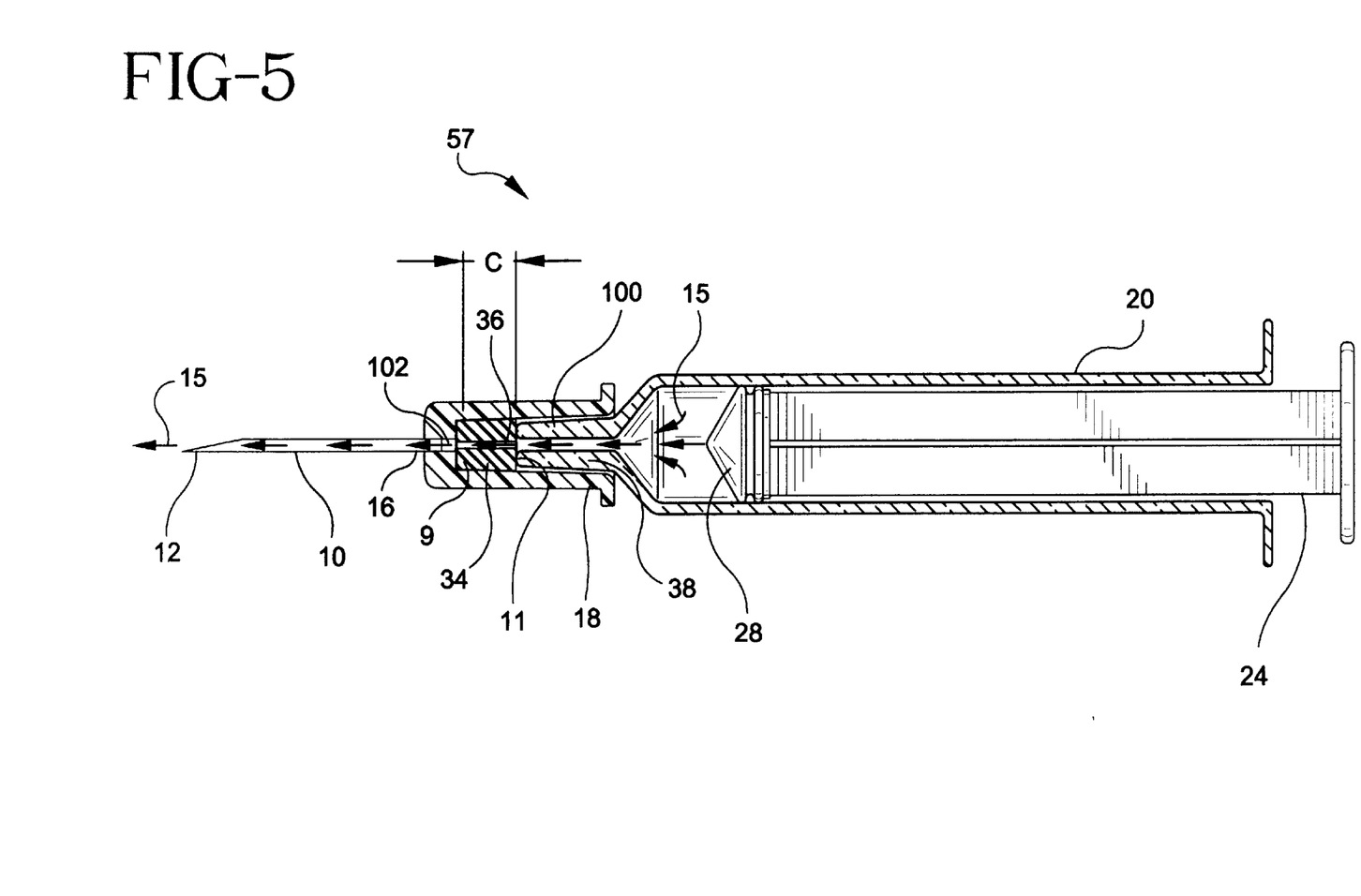
FIG. 5 is a longitudinal cross-sectional view of the subject invention taken along line 5—5 in FIG. 2b.

In FIGS. 3–8, the advantage of reducing dead-space volume 14 independent of manufacturing tolerances of mating components' dimensions is illustrated. Hub 18 and needle hub 118 of medication transfer connector 56 has an open end 26, a end 22 and a conduit 102 therethrough as shown in FIG. 3 and FIG. 4. The open end 26 is for receiving the first fluid transfer device 1 or syringe 171 which contains the medication to be delivered to the patient. Open end 26 has a surface 7 shown in FIG. 3 which defines a cavity 100. Preferably, the cavity 100 is conical, but does not need to be so shaped. Closed end 22 is attached to the second fluid transfer device like needle cannula 51 or piercing member 10. Conduit 102 is in fluid communication with the second fluid transfer device. Resilient member 34 for reducing dead-space volume 14 and has a first end 46, a second end 42, an outside surface 421 and a channel 36 therethrough. Resilient member 34 is disposed in the cavity 100 of the hub 18. Preferably, resilient member 34 is tapered, but does not need to be so shaped. However, it is critical that the shape of resilient member 34 and cavity 100 are so shaped as to accept resilient member 34 in cavity 100. First end 46 is exposed to cavity 100. Portions of outside surface 421 form a seal 9 about surface 7 of open end 26 such that the channel 36 is in fluid communication with the conduit 102 of hub 18. Preferably, proximal end 16 of piercing member 10 or proximal end 116 of piercing member 10 may be attached to end 22 of the hub 18. Lumen 811 is in fluid communication with conduit 102.

Figure 7:
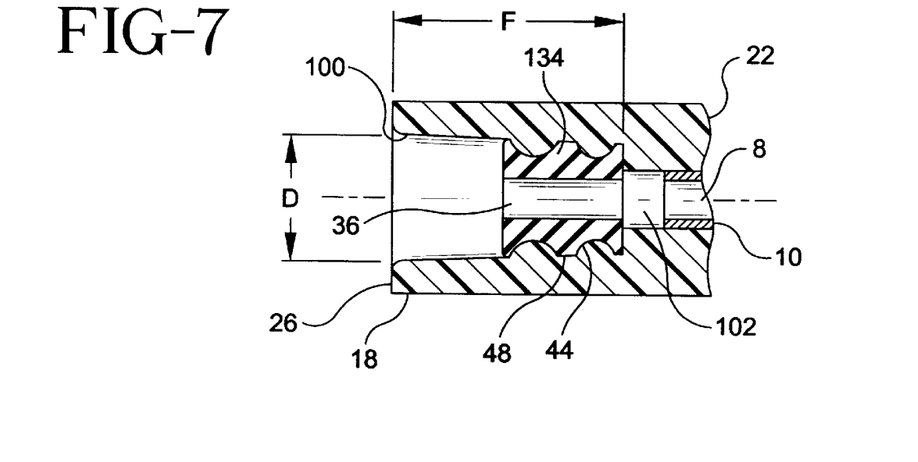
FIG. 7 is an enlarged cross-sectional view of a medication transfer connector of the subject invention.
Figure 8:
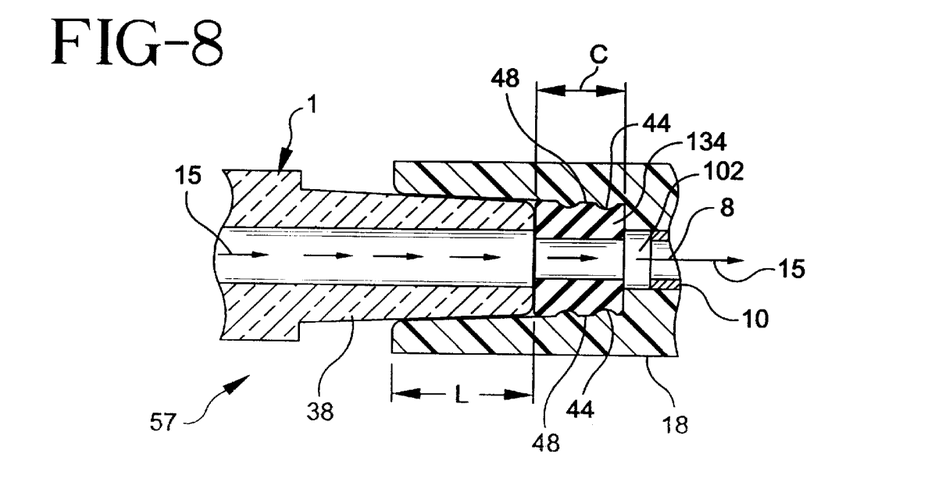
FIG. 8 is an enlarged cross-sectional view of a medication transfer connection wherein the male fitting in FIG. 6 is attached to the medication transfer connector in FIG. 7.

In FIGS. 3 and 4, when medication transfer connector 56 is attached to first fluid transfer device 1 a medication transfer connection 57 is formed. Distal to proximal movement of hub 18 onto male fitting 38 causes resilient member 34 to gradually compress from an uncompressed length "U" to a compressed length "C". A second seal 11 is formed between first end 46 of resilient member 34 and first fluid transfer device 1. Then, channel 36 is in fluid communication with fluid path 15 of first fluid transfer device 1, conduit 102, and lumen 8 of piercing member 10. Preferably, resilient member 34 is an elastomeric plug 134 as shown in FIGS. 7–8.

The present invention's primary function is to reduce the dead-space volume 14 between medical transfer connector 56 and first fluid transfer device 1 while not depending on control of the manufacturing tolerances of their mating components' dimensions. The present invention also allows reduction of dead-space volume 14 in other medical components made from different medical device manufacturers.

Different manufacturers operate under different manufacturing tolerances. Mixing first fluid transfer device and hub components from different manufacturers compound the problem of reducing dead-space volume 14 because of this variation in tolerances. However, the use of the resilient member 34 with either hub 18 or needle hub 118 or first fluid transfer device 1 or syringe 171 as shown in FIGS. 3–11 allows reduction of dead-space volume 14 between medical transfer connectors and first fluid transfer devices of different manufacturers. This feature can be achieved because reduction of dead-space volume 14 in the present invention does not totally depend on the control of manufacturing tolerances of the mating components' dimensions. Thus, selection and interchange of components are allowed.

Manufacturing tolerances of the mating components' dimensions are further examined below. As shown in FIGS. 4–8, the resilient member 34 or elastomeric plug 134 compresses when male fitting 38 is inserted into the cavity 100 of hub 18 or needle hub 118. This compression allows variations in the manufacturing tolerances of the respective mating components' dimensions. There are many mating components' dimensions that give rise to the amount of dead-space volume 14. The following dimensions for mating components are given as an example and are not meant to limit the scope of the present invention. It is within the purview of the present invention to be independent of any dimension or dimensions manufacturing tolerances that are related to the creation of dead-space volume 14. The first fluid transfer device 1 includes male fitting 38. The male fitting 38 has a minor diameter "A" and an overall length "E". The medical transfer connector 56 includes a hub 18, which has an inside diameter "D", and a length "F". Resilient member 34 or elastomeric plug 134 compresses, when male fitting 38 is inserted an insert length "L", to the appropriate compressed length "C" based on the pre-existing tolerances of the mating components. Thus, dead-space volume 14 is reduced independent of controlling the manufacturing tolerances of the mating component dimensions like dimensions "A", "E", "F", "D", "C" and "L". This reduction is possible regardless of the tolerances of these dimensions, or any other dimension that is critical to the mating of male fitting 38 of first fluid transfer device 1 and cavity 100 of hub 18.

Resilient member 34 and elastomeric plug 134 are contained within hub 18 to form the medical transfer connector 56. Preferably, resilient member 34 is attached to hub 18. There are many ways known to one skilled in the art to attach resilient member 34 to hub 18. These methods include, but are not limited to, snap fit structures, adhesives, heat or sonic welding, and various injection molding techniques such as co-injection molding.

The following attachment method is considered exemplary of these many possibilities. It is within the purview of the present invention to include any of these attachment methods or other attachment methods known to one skilled in the art. However, it is critical that the attachment method chosen does not interfere with the elastic properties of the resilient member 34 or elastomeric plug 134. This feature is critical to the present invention because it is the elastic properties of the resilient member 34 and elastomeric plug 134 that is responsible for the independence of the manufacturing tolerances. There are many ways to characterize the elastic properties. One common method is by denoting the material's modulus of elasticity or flexural modulus. The flexural modulus is a measure of the material's stiffness during bending and is calculated by dividing the change in stress by the corresponding change in strain. Preferably, the resilient member 34 and elastomeric plug 134 would have a flexural modulus typical of elastomeric materials.

A method of attachment of resilient member 34 and elastomeric plug 134 to hub 18 would include the following features. Cavity 100 may be conical and resilient member 34 and elastomeric plug 134 may be tapered so as to be held in cavity 100 by a frictional or press-fit. As described above, there are many ways to connect resilient member 34 or elastomeric plug 134 to hub 18 or needle hub 118 including snap-fit structure, adhesives, welding, two-shot molding and other assembly method known to one skilled in the art. The press-fit arrangement described above is considered exemplary of these many possibilities.

Figure 6:
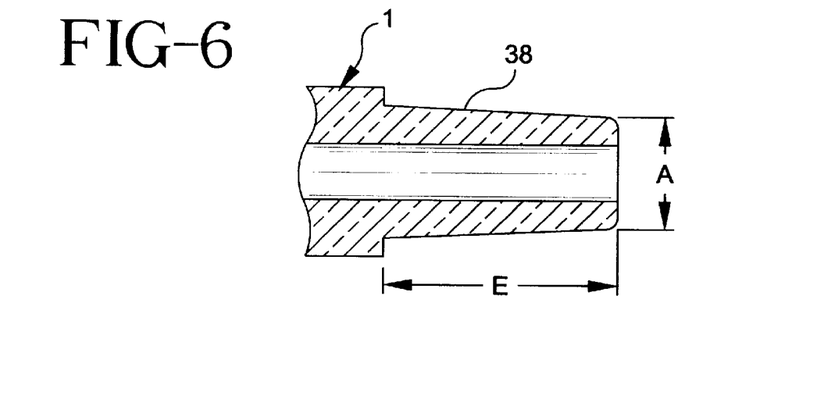
FIG. 6 is an enlarged cross-sectional view of a male fitting of a first fluid transfer device.

A preferred embodiment, as shown in FIGS. 6–8, has a elastomeric plug 134 comprising of at least one external locking rib 48. Surface 7 of open end 26 of hub 18 could comprise at least one internal locking rib 44. Having external locking rib 48 and internal locking rib 44 adjacent to each other would facilitate mounting of the elastomeric plug 134 to hub 18. This attachment method may be advanced even more by incorporating the press-fit method described above where in this case cavity 100 may be conical and elastomeric plug 134 may be tapered so as to also be held in cavity 100 by a frictional or press-fit.

Figure 9:
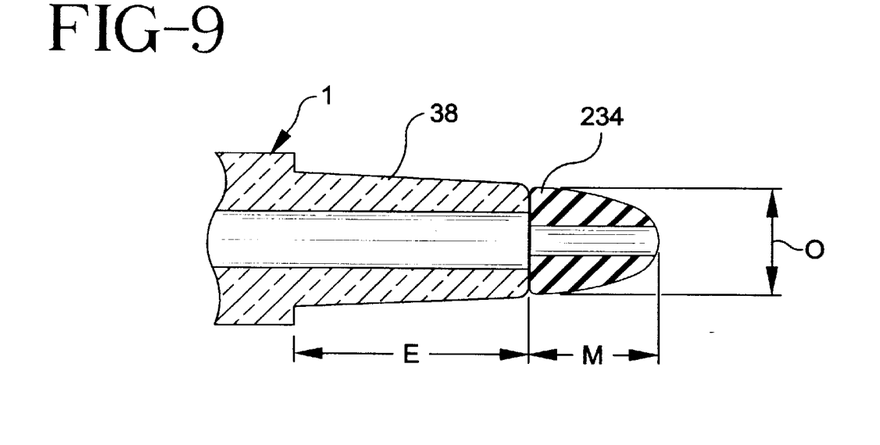
FIG. 9 is an enlarged cross-sectional view of a resilient member attached to a first fluid transfer device.
Figure 10:
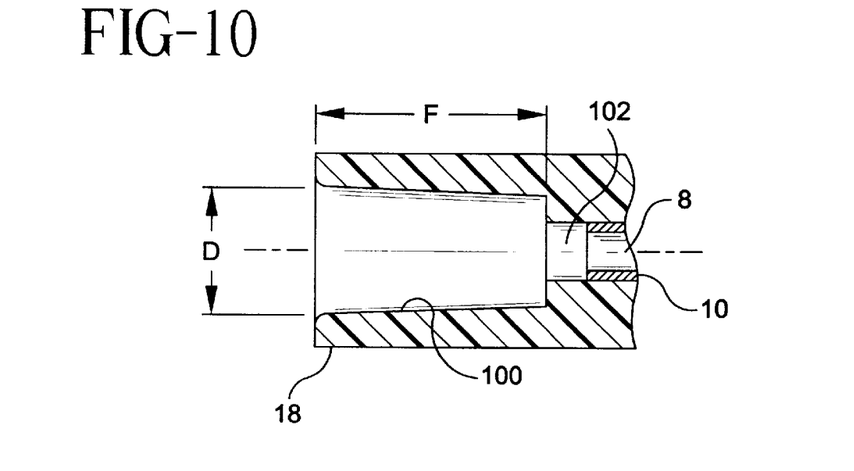
FIG. 10 is an enlarged cross-sectional view of a matching hub for FIG. 9.
Figure 11:
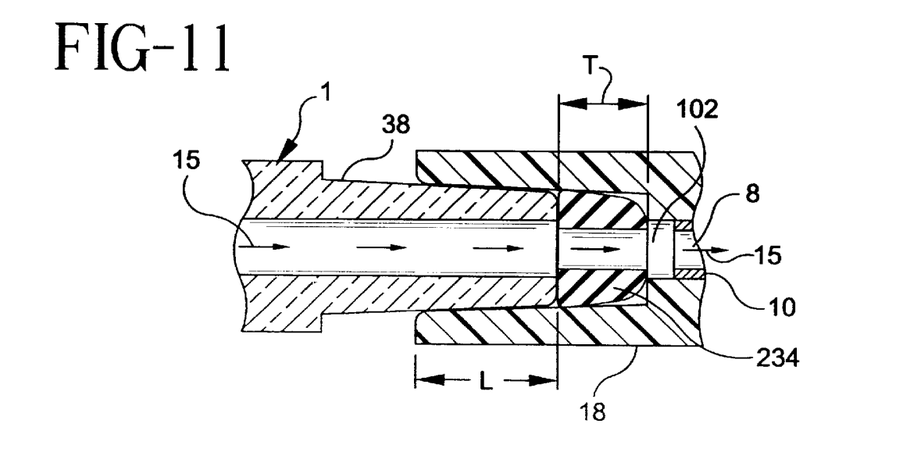
FIG. 11 is an enlarged cross-sectional view of an alternate embodiment of the present invention where the male fitting in FIG. 9 is attached to the hub in FIG. 10.

FIGS. 9–11 illustrate another embodiment of the present invention where a resilient member 234 is fixably attached to the first fluid transfer device 1. Again, there are many methods of assembly known to one skilled in the art to attach resilient member 234 to first fluid transfer device 1. It is within the purview of this invention to include all such attachment methods. In the above alternative embodiment resilient member 234 is fixably attached to the first fluid transfer device 1. Resilient member 234 has an original length "M" and an outside major diameter "O". A compacted length "T" is created when resilient member 234 is gradually compressed when male fitting 38 is inserted an insert length "L" into cavity 100. Thus, reduction of dead-space volume 14 is independent of the manufacturing tolerances of dimensions "E", "O", "M", "F", "D", "L" and "T", or any other dimensions critical to the mating of cavity 100 of hub 18 and male fitting 38 of first fluid transfer device 1. As stated previously, the resilient member 234 compensates by compressing appropriate length "T" while reducing dead-space volume 14 in fluid path 15.

In this alternate embodiment, resilient member 234 like resilient members 34 and elastomeric plug 134 would be made out of an elastomeric material. The elastomeric material may include natural rubber, thermoplastic rubber (TPR), ethylene propylene diene monomer (EPDM), Styrene-butadiene rubber (SBR), neoprene, nitrite rubber, polyisoprene, ethylene propylene copolymer (EPM), ethylene propylene rubber (EPR), silicone rubber, thermoplastic elastomers etherether (TEEE), thermoplastic elastomer olefinic (TEO), thermoplastic elastomer styrene (TES), thermoplastic urethane, thermoplastic polyolefinic elastomer (TPO) and other thermoplastic elastomers (TPE).

Figure 12:
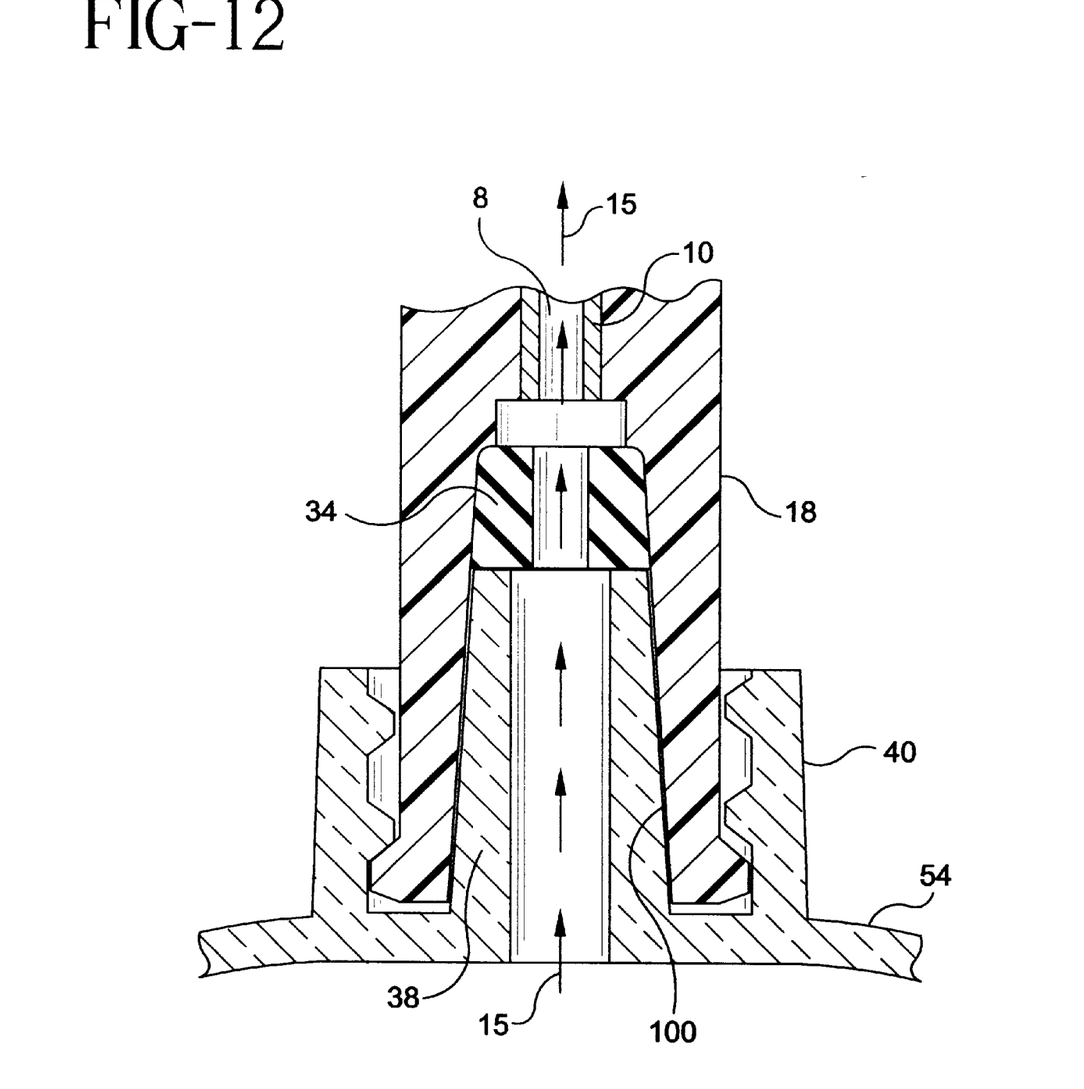
FIG. 12 is an enlarged cross-sectional view of an alternative embodiment of the subject invention.

FIG. 12 demonstrates another alternative embodiment. In this Figure, male fitting 38 is on an alternate embodiment of a first fluid transfer device 54. First fluid transfer device 54 in this embodiment may be an I.V. bag or assembly, an insulin pump, an injector pen, a syringe or any other medical device which delivers medication through a connector that creates dead-space volume 14 in its fluid path 15 to the patient.

In this alternate embodiment, first fluid transfer device 54 contains a male locking means 40 to hold hub 18 in place. With this arrangement, resilient member 34 is secured in cavity 100 without any internal means of attachment. Thus, resilient member 34 need not be fixably attached to either the cavity 100 or the first fluid device 54 for the present invention to be used. The resilient member 34 need only be placed in cavity 100 or on male fitting 38 of first fluid transfer device 54 to be able to reduce dead-space volume 14 in fluid path 15.

However, it is preferred to have the resilient member 34 fixably attached to cavity 100 to reduce the possibility of resilient member 34 disengaging from cavity 100 before connection is completed.

Figure 13:
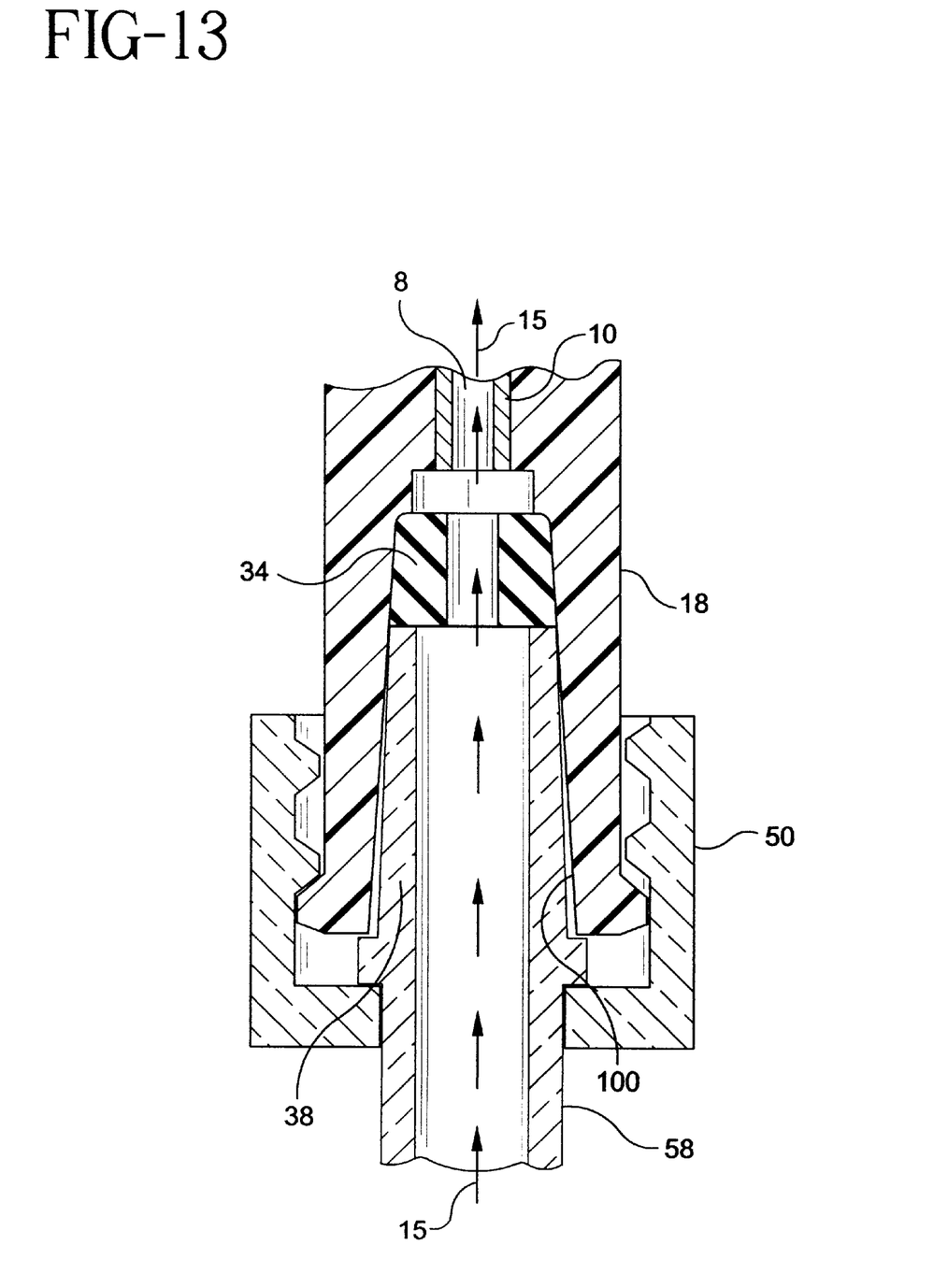
FIG. 13 is an enlarged cross-sectional view of another alternative embodiment of the subject invention.

FIG. 13 illustrates another alternate embodiments of the male fitting 38 on an alternate embodiment of a first fluid transfer device 58. The first fluid transfer device 58 in this embodiment may be an intravenous or stopcock assembly. However, it is within the purview of the present invention that the first fluid transfer device 58 may be an I.V. bag or assembly, an insulin pump, an injector pen, a syringe or any other medical device which delivers medication through a connector that creates dead-space volume 14 in its fluid path 15 to the patient.

The first fluid transfer device 58 includes a locking means 50 which may be used if resilient member 34 is not fixably attached to either cavity 100 or first fluid transfer device 1. Again, this arrangement allows resilient member 34 to be secured in cavity 100 without any internal means of attachment.

Figure 14:
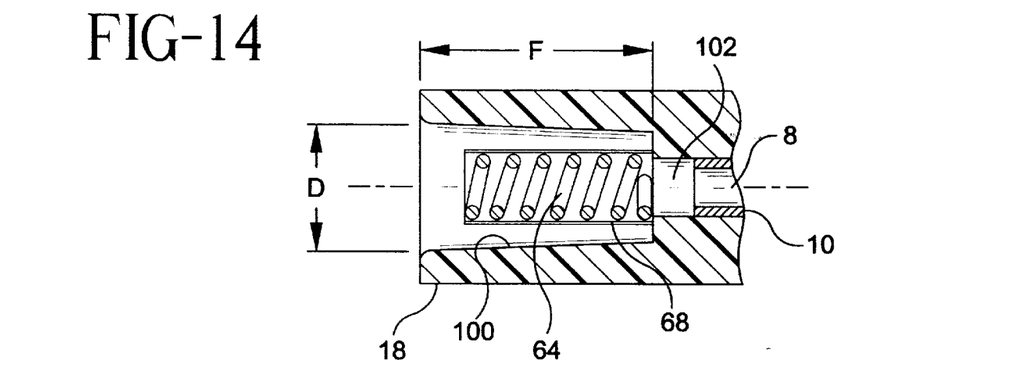
FIG. 14 is an enlarged cross-sectional view of an alternative medication transfer connector where a resilient member is a coil spring assembly.
Figure 15:
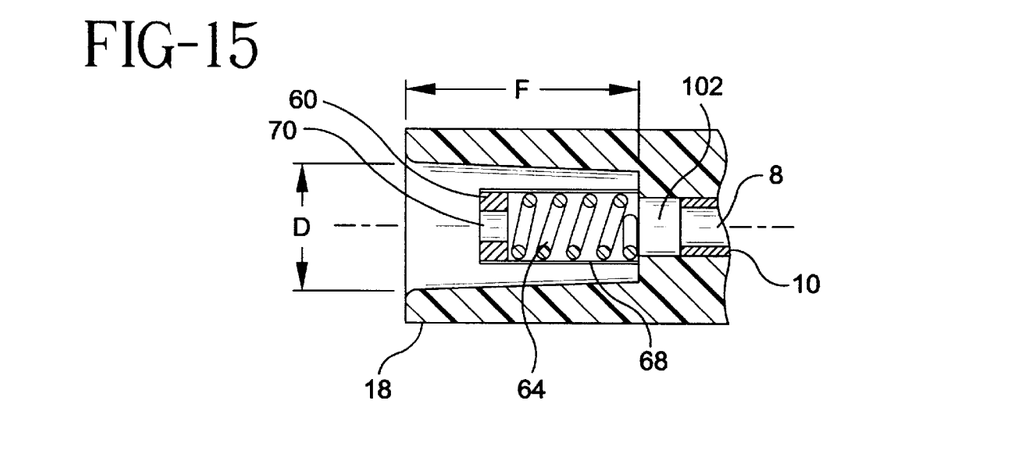
FIG. 15 is an enlarged cross-sectional view of another alternative medication transfer connector where the resilient member is a coil spring assembly with a locating ring.
Figure 16:
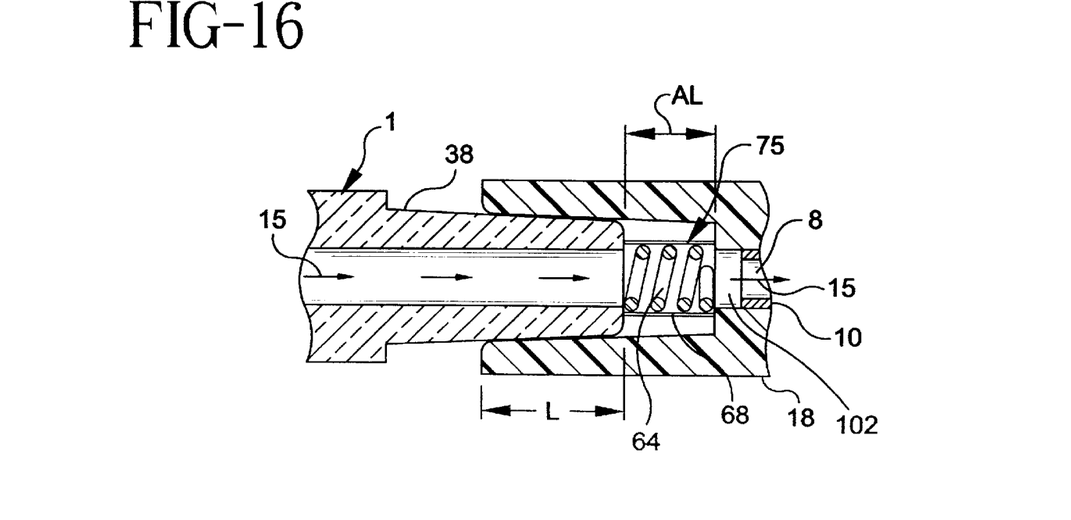
FIG. 16 is an enlarged cross-sectional view of an alternative embodiment of the present invention where the male connector in FIG. 6 is attached to the medication transfer connector in FIG. 14.

FIGS. 14–19 illustrate another alternate embodiment for the medication transfer connector 56 and connection 57. In this embodiment, resilient member 34 is a coil spring assembly 75. Coil spring assembly 75 comprises a coil spring 64 and a resilient sheath 68. Resilient sheath 68 covers coil spring 64. Preferably, coil spring assembly 75 would also include a locating ring 60 with a passage 70 therethrough. The purpose of locating ring 60 is for locating the fluid path 15 or first fluid transfer device 1. The use of locating ring 60 is preferred but not required for the present invention to function. As shown in FIG. 16, coil spring assembly 75 can be used without locating ring 60. Locating ring 60 makes it easier to locate fluid path 15 or first fluid transfer device 1 when hub 18 is assembled onto male fitting 38 of first fluid transfer device 1. When locating ring 60 is used during this assembly procedure, passage 70 of locating ring 60 is in fluid communication with fluid path 15 of first fluid transfer device 1 and conduit 102 and lumen 8. Conduit 102 of hub 18 is in fluid communication with lumen 8 of piercing member 10. This alternate embodiment can also be used with needle hub 118 in FIG. 3. In this embodiment, conduit 102 of needle hub 118 is in fluid communication with lumen 811 of piercing member 10.

Coil spring assembly 75 is fixably attached to hub 18. Again, there are many ways to connect coil assembly 75 to hub 18 including press-fit structures, snap-fit structures, adhesives, welding, two-shot molding and other methods of assembly known to one skilled in the art. It is within the purview of the present invention to include all these methods. Additionally, as stated with resilient member 34, 234 and elastomeric plug 134, coil spring assembly 75 need not be fixably attached for the present invention to be used. It is preferred that coil spring assembly 75 be attached to reduce the possibility of coil spring assembly 75 from dislodging before connection of hub 18 to male fitting 38 of the first fluid transfer device 1 is completed.

When hub 18 is attached to first fluid transfer device 1, medication delivered by first fluid transfer device 1 flows through coil spring 64 and resilient sheath 68 prevents the medication from escaping. Resilient sheath 68 guides the medication through conduit 102 of the hub 18 to the second fluid transfer device. Again, it is preferred that the second fluid transfer device is piercing member 10. However, it can be piercing member 10 having the lumen 8. Conduit 102 is in fluid communication with the lumen 8 or lumen 811 as shown in FIG. 6 and FIG. 3.

Manufacturing tolerances of the mating components' dimensions, the hub 18 and male fitting 38, are overcome by the compression of coil spring 64 which adapts to an appropriate length "AL" based on the given manufacturing tolerances of the mating components critical dimensions.

Preferably, the embodiment as described above would contain locating ring 60 with the passage 70. Locating ring 60 would be adjacent to coil spring 64. Passage 70 is in fluid communication with conduit 102 of hub 18. If FIG. 15 was assembled to FIG. 6 instead of FIG. 6 assembled with FIG. 14, as shown in FIG. 16 fluid path 15 of first fluid transfer device 1 would consist of first fluid transfer device 1, passage 70, coil spring assembly 75, conduit 102, and lumen 8.

Figure 17:
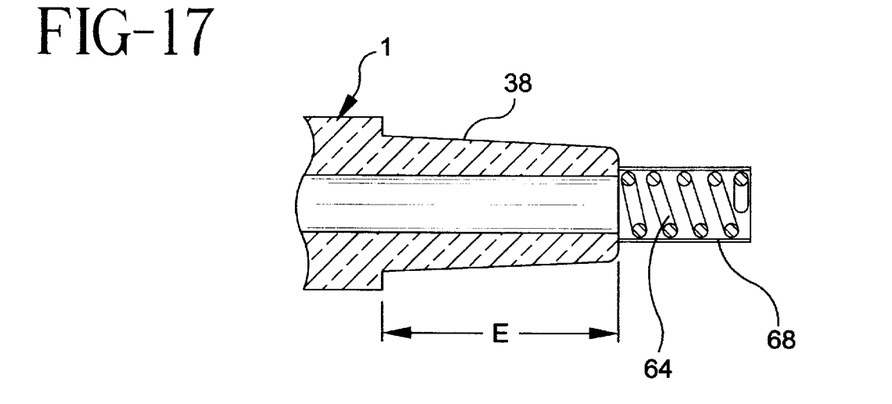
FIG. 17 is an enlarged cross-sectional view of a coil spring assembly attached to a first fluid transfer device.
Figure 18:
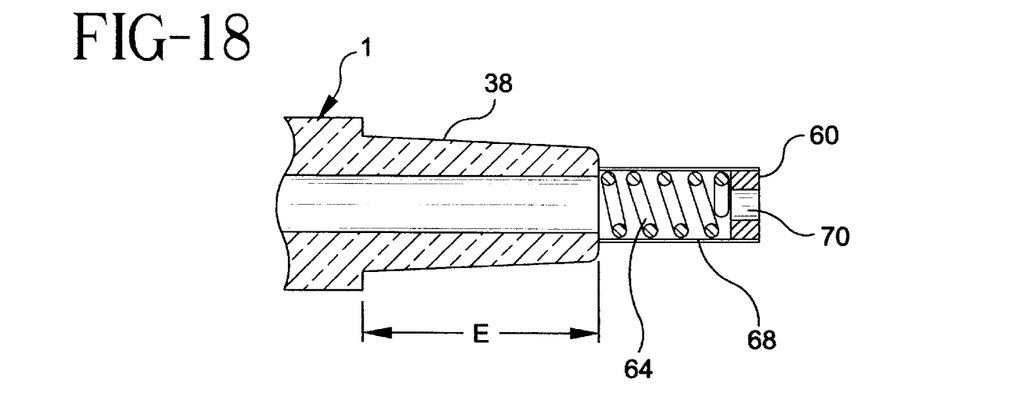
FIG. 18 is an enlarged cross-sectional view of a first fluid transfer device attached to a coil spring assembly with a locating ring.
Figure 19:
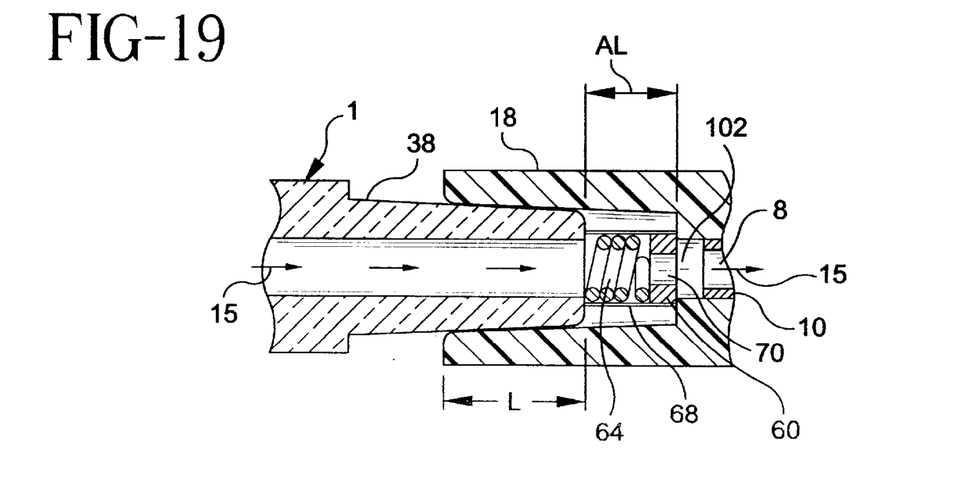
FIG. 19 is an enlarged cross-sectional view of an alternative embodiment of the present invention with the male fitting in FIG. 18 attached to the hub in FIG. 10.

FIGS. 17–19 illustrate an alternate embodiment of FIGS. 14–16 where the resilient member 34 is replaced with coil spring assembly 75. In this alternate embodiment, coil spring assembly 75 is fixably attached to first fluid transfer device 1 instead of hub 18. Again, coil spring assembly 75 need not be fixably attached for the present invention to function. However, it is preferred to avoid dislodgment of coil spring assembly 75.

Coil spring assembly 75 in this alternate embodiment may also include a locating ring 60 which has a passage 70 therethrough. Locating ring 60 in this embodiment functions by aligning fluid path 15 of first fluid transfer device 1 and coil spring assembly 75 with conduit 102 of hub 18.

Again, it is not necessary for coil spring assembly 75 to be fixably attached to first fluid transfer device 1. Coil spring assembly 75 could alternatively be placed either on first fluid transfer device 1 or inside cavity 100 of hub 18. However, it is preferred that coil spring assembly 75 be fixably attached inside cavity 100 of hub 18 for purposes of reducing the possibility of coil spring assembly 75 being dislodged before connection.

The medication transfer connector 56 and connection 57 will still effectively operate regardless of whether or not resilient member 34, or 234 or elastomeric plug 134 or coil spring assembly 75 is fixably attached to cavity 100 or in the alternative to first fluid transfer device 1. However, in these alternate embodiments, placement of resilient member 34, or 234 and elastomeric plug 134 or coil spring assembly 75 is critical. Alignment of channel 36, or passage 70 for use with coil spring assembly 75, to conduit 102 is critical to maintain fluid path 15 between first fluid transfer device 1 and second fluid transfer device or piercing member 10 or piercing member 10. Again, it is preferred that, the second fluid transfer device would be piercing member 10 with lumen 811. In the previously described preferred embodiment, the lumen 811 of piercing member 10 would be in fluid communication with the fluid path 15 of the first fluid transfer device 1.

What is claimed is:

1. A medication transfer connection that reduces dead-space volume, comprising:
    a syringe for delivering medication;
    a needle cannula having a proximal end, a sharpened distal end and a lumen therethrough;
    a needle hub having an open end, and an end having a conduit therethrough, said open end for receiving said syringe and having a surface defining a cavity, said proximal end of said needle cannula attached to said conduit such that said conduit is in fluid communication with said lumen; and
    an elastomeric plug having a first end, an outside surface, and a channel therethrough, said plug disposed in said cavity, said channel in fluid communication with said conduit and uniformly sized smaller than said conduit such that said channel provides for minimization of medication in said elastomeric plug, said syringe is in fluid communication with said channel when said syringe received in said open end and said plug compressed for reducing dead-space volume independent of dimensional tolerances of said hub and said syringe.

2. A medication transfer connector for reducing dead-space volume, comprising:
    a hub having an open end and an end having a conduit therethrough, said open end having a surface defining a cavity; and
    a resilient member having a first end, an outside surface, and a channel therethrough, said resilient member disposed in said cavity for reducing dead-space volume, said channel is in fluid communication with said conduit and uniformly sized smaller than said conduit such that said channel provides for minimization of medication in said resilient member, a piercing member having a proximal end, a distal end and a lumen therethrough, said proximal end attached to said conduit such that said lumen is in fluid communication with said conduit.

3. The medication transfer connector of claim 2, wherein said piercing member is a needle cannula.

4. The medication transfer connector of claim 3, wherein said needle cannula was a sharpened distal end.

5. The medication transfer connector of claim 2, wherein portions of said outside surface form a seal about said surface of said open end.

6. The medication transfer connector of claim 2, wherein said resilient member is made of an elastomeric material.

7. A medication transfer connection that reduces dead-space volume in a fluid path, comprising:
    a syringe for delivering medication;
    a piercing member having a proximal end, a distal end, and a lumen therethrough;
    a hub having an open end, and an end having a conduit therethrough, said open end for receiving said syringe and having a surface defining a cavity, said proximal end of said piercing member attached to said conduit such that said conduit in fluid communication with said lumen; and
    an elastomeric plug having a first end, an outside surface, and a channel therethrough, said elastomeric plug disposed in said cavity for reducing dead space volume, said channel is in fluid communication with said conduit and uniformly sized smaller than said conduit such that said channel provides for minimization of medication in said resilient member.

8. The medication transfer connection of claim 7, wherein said piercing member is a needle cannula.

9. The medication transfer connection of claim 8, wherein said needle cannula has a sharpened distal end.

10. The medication transfer connection of claim 7, wherein portions of said outside surface form a seal about said surface of said open end.

11. The medication transfer connection of claim 7, wherein said resilient member compresses in said cavity when said syringe received in said open end for reducing dead space volume independent of dimensional tolerances of said hub and said syringe.

* * * * *